United States Patent
Göthe et al.

[19]

[11] Patent Number: 5,873,991
[45] Date of Patent: Feb. 23, 1999

[54] METHOD FOR ELECTROPHORETIC SEPARATION

[75] Inventors: Sven Göthe, Bromma; Anders Hult, Täby; Jan-Olof Johansson, Knivsta; Lennart Kågedal; Anna Sylwan, both of Upsala, all of Sweden

[73] Assignee: Pharmacia Biotech AB, Upsala, Sweden

[21] Appl. No.: 831,929

[22] Filed: Apr. 2, 1997

[30] Foreign Application Priority Data

Dec. 20, 1996 [SE] Sweden .................................. 9604730

[51] Int. Cl.[6] ..................................... G01N 27/26
[52] U.S. Cl. ......................... 204/470; 204/469; 204/470; 204/606
[58] Field of Search ................... 207/456, 465, 207/469, 470, 606, 615

[56] References Cited

FOREIGN PATENT DOCUMENTS

| 0169397B1 | 1/1986 | European Pat. Off. . |
| WO97/ 17384A1 | 5/1997 | WIPO . |

*Primary Examiner*—Robert Warden
*Assistant Examiner*—Alex Naguerda

*Attorney, Agent, or Firm*—Birch, Stewart, Kolasch & Birch, LLP

[57] ABSTRACT

Method for electrophoretic separation of nucleic acid fragments comprising the following steps:

a) providing a polyacrylamide based gel prepared by photoinitiated polymerization of a mixture containing monoolefinic- and di- and/or polyolefinic monomers and a photoinitiator of the general formula:

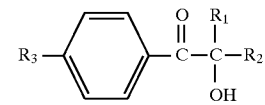

where $R_1$ and $R_2$ independently are $CH_3$, $C_2H_5$ or $C_3H_7$ or $R_1$, $R_2$ together with the carbon atom form a cycloaliphatic ring with 4–8 carbons;

$R_3$=H, $CH_3$, $C_2H_5$ or $-O-(CH_2CH_2)_n-OH$ with n=1–20;

b) applying said nucleic acid fragments on said polyacrylamide based gel;

c) electrophoretically separating said fragments on said gel. The invention also relates to a kit for use in the method for electrophoretic separation of nucleic acid fragments.

9 Claims, 4 Drawing Sheets

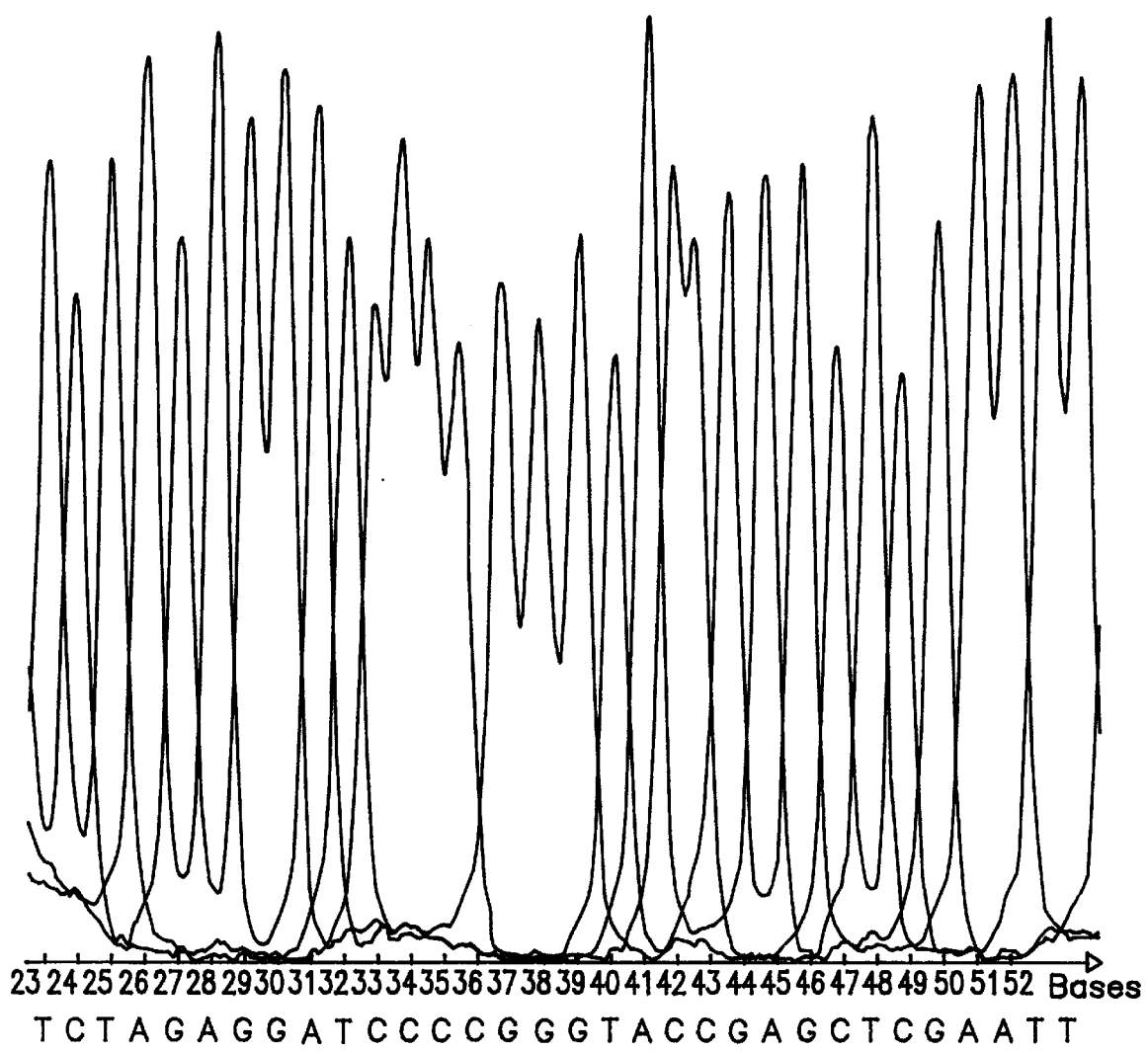

METHOD FOR ELECTROPHORETIC SEPARATION

The present invention relates to a method for electrophoretic separation of nucleic acid fragments and a kit for use in the method. In particular the invention relates to separation on polyacrylamide based gels prepared by photoinitiated polymerization.

Gel electrophoresis is today a widely used method for separating biomolecules. The method is routinely used for separating proteins, peptides, nucleic acids etc., often with automated equipment based on fluorescence detection. One important application is separation of nucleic acid fragments e.g. obtained in DNA sequencing. Several automated systems for DNA sequencing are available in the market.

Gel electrophoretic separation of molecules is based on the difference in charge density of the different molecules as well as the sieving effect of the porous gel media. The extent of sieving depends on how well the pore size of the gel matches the size of the migrating molecules. Different types of gel material are used, for example dextrane, agarose and polyacrylamide. Polyacrylamide gels are commonly used due to their good qualities. Polyacrylamide can be prepared in a reproducible manner, with a wide range of pore sizes. Besides, the polyacrylamide gels are chemically inert, stable over a wide range of pH and temperatures and they are transparent.

The electrophoretic gel is composed of a network of cross-linked polymer molecules which forms the pores of the gel. The separating qualities of the gel depend on, among other things, how big and how evenly distributed the pores of the network are. The size and the distribution on the other hand, are dependent on the dry solids content of the gel, on the content of cross-linker and on the method of initiation.

The gel based on polyacrylamide is made by polymerization of a monooloefinic monomer, such as acrylamide, with a bifunctional monomer such as methylene bisacrylamide. The polymerization can be initiated either chemically e.g. by sodium or ammonium persulfate and tetramethylethylenediamine or photochemically. There are several disadvantages with the chemically initiated polymerization. The polymerization is strongly inhibited by oxygen as the free radical production is slow. As it is difficult to know the oxygen content of the gel casting solution it is impossible to obtain a well defined degree of monomer conversion. The structure of the polymer network will vary from one gel casting to another, resulting in a bad reproducibility. Further, with the initiator, charged sulfate groups are introduced into the polymer network, which creates electroendosmosis. As the reaction starts immediately after the mixing of the components a rather quick application of the reaction mixture into the gel mold is required.

To avoid the above mentioned disadvantages, gels made by photoinitiated polymerization have been proposed. Riboflavin or riboflavin 5'-phosphate in combination with an amine has been used since the 1950's, but requires long irradiation times and tends to give lower conversion than chemical initiation as mentioned above.

EP 169 397 relates to an improved method for preparing photoinitiated electrophoresis gels. The process is based on photoinintiation with initiator systems such as benzoin ethers, benzophenone derivatives and amines, phenantrenequinones and amines, naphtoquinones and amines, methylene blue and toluene sulfinate. With these initiators a faster polymerization is obtained. Still however, the quantum efficiency, i.e. the amount of radicals produced per absorbed photon, for these initiators is very low. The majority of them are also charged species which increase the ionic strength of the gels. This causes the gel resistance to vary with time during electrophoresis, which in automatic DNA sequencing gives varying distances between the peaks and thus complicates the automatized peak detection.

For many electrophoretic applications the gels used are ready made gels cast by a supplier. For sequencing separation of nucleic acids however, it is difficult to use ready made gels. This is due to the fact that the denaturing agent used to separate double stranded DNA, mostly urea, is not stable in the water containing gel, but forms ionic systems. Thus, it is not possible to use the commercially available gels for e.g. protein separation, for DNA sequencing separation. The gels for nucleic acid separation are therefore usually cast by the user at the moment of separation. The predominant method today for initiation of gel solutions for DNA fragment separation is by chemical initiation. For the gel casting the user has to mix the gel solution and the initiator, remove oxygen and quickly cast the solution as the initiation starts immediately. Still the other drawbacks mentioned above are achieved.

There is therefore a need for an improved method for the production of electrophoretic gels for separation of nucleic acid fragments. There is also a need for improved methods of photoinitiation of acrylamide polymerization for electrophoresis gel production in general.

The object of the present invention is to obtain an improved method for electrophoretic separation of nucleic acid fragments.

A further object of the invention is to provide an electrophoretic gel for use in electrophoretic separation of nucleic acid fragments.

Yet a further object of the invention is to present an improved gel kit for use in the production of electrophoretic gels.

The objects of the invention are achieved by the method for electrophoretic separation of nucleic acid fragments and the kit for use in the method, as claimed in the claims.

According to the invention a method for electrophoretic separation of nucleic acid fragments is obtained. The method comprises the following steps:

a) providing a polyacrylamide based gel prepared by photoinitiated polymerization of a mixture containing monoolefinic- and di- and/or polyolefinic monomers and a photoinitiator of the general formula:

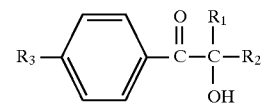

where $R_1$ and $R_2$ independently are $CH_3$, $C_2H_5$ or $C_3H_7$, or $R_1$, $R_2$ together with the carbon atom form a cycloaliphatic ring with 4–8 carbons;

$R_3$=H, $CH_3$, $C_2H_5$ or $-O-(CH_2CH_2)_n-OH$ with n=1–20;

b) applying said nucleic acid fragments on said polyacrylamide based gel;

c) electrophoretically separating said fragments on said gel.

The invention also comprises a kit for use in a method for electrophoretic separation of nucleic acid fragments on a polyacrylamide based gel. The kit comprises:

(i) a mixture of monoolefinic- and di- and/or polyolefinic monomers, (ii) optionally buffer and denaturing agent,
(iii) a photo initiator with the general formula:

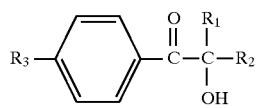

where
R$_1$ and R$_2$ independently are CH$_3$, C$_2$H$_5$ or C$_3$H$_7$ or R$_1$, R$_2$ together with the carbon atom form a cycloaliphatic ring with 4–8 carbons;
R$_3$=H, CH$_3$, C$_2$H$_5$ or —O—(CH$_2$CH$_2$)$_n$—OH with n=1–20.

With the present invention it was found that by preparing the gel by photopolymerization with special initiators an improved separation method was obtained. For the prepared gel the content of residual monomers was minimized and a faster and more complete polymerization was obtained. In DNA sequencing separation, where the user has to cast the gel, the fast polymerization is especially advantageous. The user will have a gel, ready for use, after about 10 minutes compared with about 2 hours for chemically initiated gels. The photoinitiated polymerization with the photo initiators used also results in a gel which is very uniformly polymerized. This is important when analyzing DNA fragments, e.g. DNA sequencing products, as this analysis means comparison of samples that have migrated in different places in the gel. The fluorescence based detection which is used today in sequencing analysis adds further unique demands on the electrophoresis gel. The gel has to be totally transparent. The detection is made with a laser beam and in some instruments the laser is situated at one side of the gel. The beam then has a long way to go through the total width of the gel. A small turbidity in the gel will result in light scattering and a too low intensity of the light when the beam reaches the bands at the farthest end. The optical homogeneity and the separation qualities of the gel are also very important in connection with laser detection. Local gradients in the refractive index result in the beam deflecting and the detection will be incorrect. The demands on the separation qualities of the gel are much higher in automated DNA sequencing or automated DNA fragment analyzis with laser detection than in ordinary gel electrophoresis. In ordinary electrophoresis the samples are run to the end of the gel and then the gel is taken out and developed. In an automated equipment the laser reads the bands at a fixed distance. This means that the electrophoresis has to be run for a long time to enable all fractions to reach the laser. Then it is important that the bands do not drift aside and miss the laser or the detectors. The computerized analysis of the result, which is used in some instruments, is based on that the bands are produced with the same distance between them. To obtain that the current/voltage ratio has to be constant. The demands, as mentioned above, are fulfilled in an improved manner by the gels used in the method of the invention compared with the gels used in the state of the art methods. One reason for the good result is believed to emanate from the high quantum efficiency of the initiators, an efficiency much higher than for the state of the art initiators. Also the fact that the gel system is completely without immobilized charged groups adds to the quality.

Thus, the initiators used in the present invention for the preparation of the gels are especially useful for casting gels for separation of nucleic acid fragments. A preferred embodiment is use of the photoinitiated gels in automated DNA sequencing, especially with fluorescence based detection. However, the method according to the invention is also suitable for gel-based separation techniques for nucleic acid fragments such as for example single stranded conformation polymorphism (SSCP).

The electrophoretic gels used in the invention, based on polyacrylamide, are produced by co-polymerization of monoolefinic monomers with di- or polyolefinic monomers. The co-polymerization with di- or polyfunctional monomers results in cross-linking of the polymer chains and thereby the formation of the polymer network. As monoolefinic monomers used in the invention can be mentioned acrylamide, methacrylamide and derivatives thereof such as alkyl-, or hydroxyalkyl derivates, e.g. N,N-dimethylacrylamide, N-hydroxypropylacrylamide, N-hydroxymethylacrylamide. The di- or polyolefinic monomer is preferably a compound containing two or more acryl or methacryl groups such as e.g. methylenebisacrylamide, N,N'-diallyltartardiamide, N,N'-1,2-dihydroxyethylene-bisacrylamide, N,N-bisacrylyl cystamine, trisacryloyl-hexahydrotriazine. In a broader sense the expression "based on polyacrylamide" also comprises, in the present context, such gels in which the monoolefinic monomer is selected from acrylic- and methacrylic acid derivatives, e.g. alkyl esters such as ethyl acrylate and hydroxyalkyl esters such as 2-hydroxyethyl methacrylate, and in which cross-linking has been brought about by means of a compound as mentioned before. Further examples of gels based on polyacrylamide are gels made by co-polymerization of acrylamide with a polysaccharide substituted to contain vinyl groups, for example allyl glycidyl dextran as described in EP 87995. Monomers which would introduce non-desirable charges into the gel are excluded from the group defined above.

The gels used in the invention are prepared from an aqueous solution containing 2–40% (w/w), preferably 3–25% (w/w) of the monomers mentioned above. The amount of cross-linking monomer is 0,5–15%, preferably 1–7% by weight of the total amount of monomer in the mixture. The structure of the polymeric network in the gel is adjusted by adjusting these parameters. An increase of the amount of monomers, i.e. the dry content, results in a more dense network. A more dense network will also be the result if the amount of cross-linker is increased. A denser network will bring about a longer separation time but a better resolution of the separated fragments.

The initiators used in the present invention are added to the aqueous monomer solution in an amount of 0,1–10 mM, preferably 0,5–5 mM. Among initiator compounds preferred for the invention can be mentioned 1-hydroxy-cyclohexyl-phenyl-ketone:

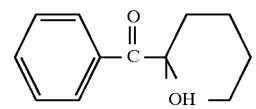

and 1-[4-(hydroxyethoxy)-phenyl]-2-hydroxy-2-methyl-1-propane-1-one:

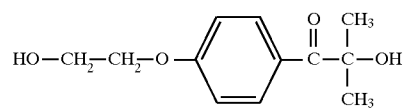

and 2-hydroxy-2-methyl-1-phenyl-propan-1-one:

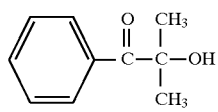

Some of the initiators in the present invention are water soluble and may thus be mixed directly with the aqueous monomer solution. Other initiators in the present invention have been used in connection with curing of lacquers, mainly in non-aqueous systems. In order to use such an initiator in an aqueous solution, the initiator is first dissolved in an organic solvent, which solvent must not adversely affect the properties of the gel when incorporated in the reaction mixture. Therefore it is important that the solubility of the initiator in the organic solvent is high enough to make it possible to use only a small amount of solvent and that the organic solvent containing the dissolved initiator is soluble in the aqueous monomer solution. As suitable organic solvents can be mentioned alcohols such as ethanol, ethylene glycol and glycerol, polyalkylene oxides, e.g. polyethyleneoxide, esters and ketones. Alternative compounds for dissolving the initiator can easily be found by the skilled man for different electrophoretic processes. For example, a monomer in a liquid state may often be useful as a solvent for the initiator.

In addition to the initiator and monomers the reaction mixture may contain various additives, the choice of which will depend on the particular electrophoretic technique contemplated. Thus, for isoelectric focusing a certain type of amphoteric compounds are added which will create a pH gradient in the gel during electrophoresis. These compounds can be charged polymer amphoteric compounds as the water-soluble ampholytes described in GB 1 596 427. Another way of obtaining a gradient of this kind is by means of amphoteric groups immobilized in the gel, as described in GB 1 570 698. This may be achieved for example by incorporating in the reaction mixture certain vinyl monomers, namely vinyl monomers containing groups capable of being charged, for example carbonic-, sulfonic- and boronic acids and phosphonic acid groups or amino groups and other nitrogen compounds capable of being charged. In the case of immunoelectrophoresis and similar techniques preparations are employed which contain antigens or antibodies as additives. Other types of additives may be buffer systems and denaturing compounds such as sodium dodecyl sulfate and urea.

The method of producing the electrophoretic gel is mainly the same if the gel is produced by a commercial supplier or by the user himself. An aqueous solution of the monomers to be used is prepared and mixed with the initiator/initiator solution and other optional additives. As the polymerization does not start until the solution is irradiated, the user of the gel can mix the initiator with the monomer solution properly, well in advance before the gel casting. It is also possible to use a ready made gel kit, which contains monomers as well as the initiator mixed in advance. The obtained cast solution is poured into a casting mould with the desired shape. The mould is ususally made of glass or of some polymer material which is transparent for UV light. The polymerization of the monomer solution is achieved by irradiating the solution with ultra-violet light. Any light source that will activate the initiators can be used. Preferred are light sources emitting light with a wave lenght within 300–400 nm. The amount of irradiation is suitably 0.5–10 joule/$cm^2$.

When very thin gels are prepared the solution is advantageously applied as a thin film on a backing material, such as a plastic film. Gels with backing can also be prepared by continuous coating processes, where the solution is applied on a moving web of plastic film.

The electrophoretic separation per see is performed by conventional methods.

BRIEF DESCRIPTION OF THE DRAWINGS

FIG. 1a represents bases in the beginning of the sequence in the gel of the invention.

EXAMPLES

Figure 1B:
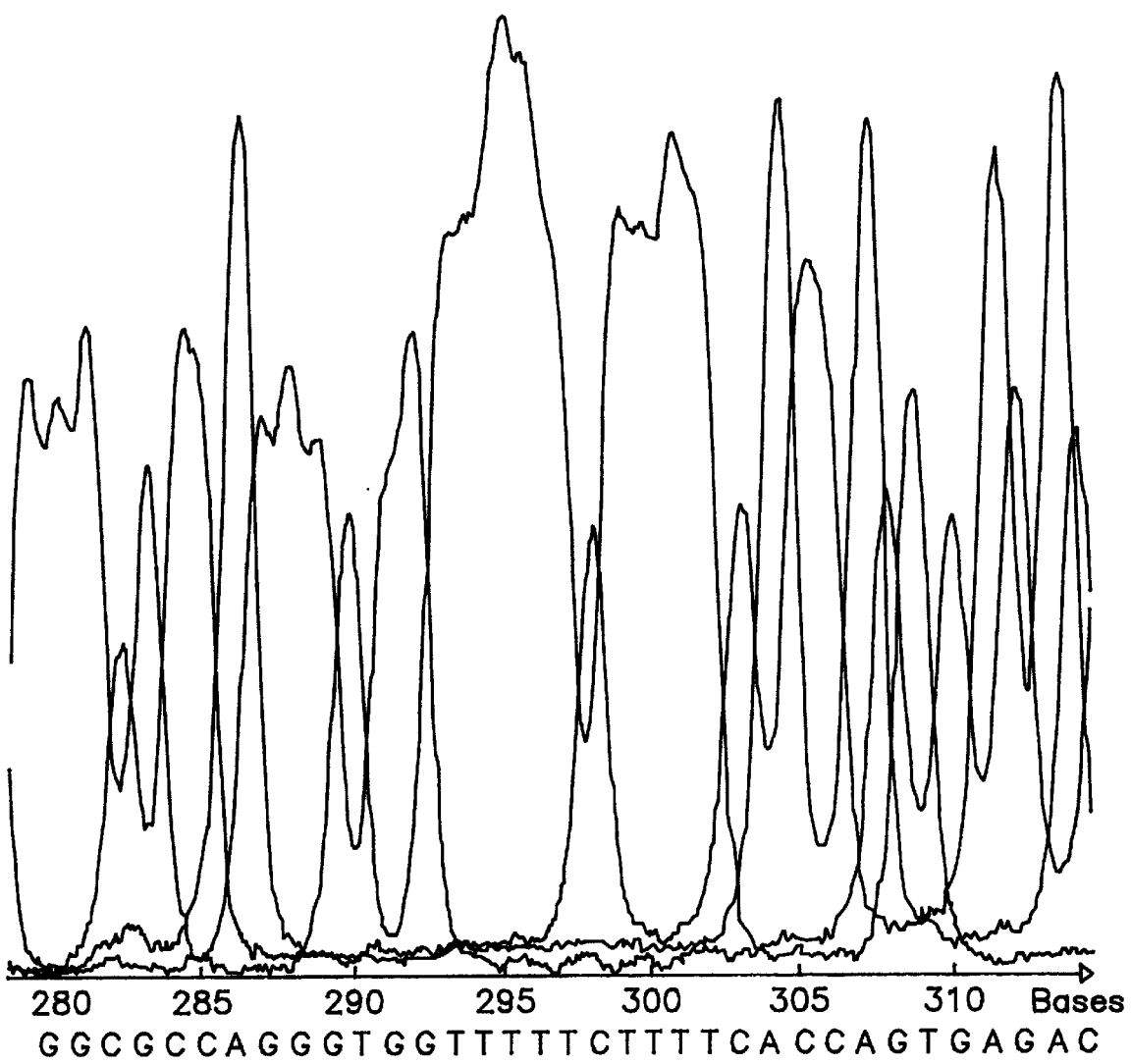
FIG. 1b represents bases further on in the sequence in the gel of the invention.

The invention will now be illustrated with the following non-limiting examples. With parts and percent are meant parts by weight and percent by weight if not differently stated.

Example 1

The following solutions were prepared:

A Monomer Stock Solution from:

300 g acrylamide 15 g methylenebisacrylamide water to obtain 1 l basic solution.

Buffer Solution:

248.28 g Tris 102,64 g Borate 7,44 g EDTA water (of high purity degree) to 2 l.

Initiator Solution:

100 mM 1-hydroxy-cyclohexyl-phenyl-ketone dissolved in ethyleneglycol.

The following components were mixed:

29 g urea, 16 ml monomer stock solution, water (of high purity degree) to obtain 60 ml.

To this mixture were added:

8 ml buffer solution 1.6 ml initiator solution water (of high purity degree) to 80 ml.

After filtration the solution was poured into a gel cassette, designed for an automated DNA sequencing equipment (ALFexpress® from Pharmacia Biotech, Uppsala) The inner surfaces of the cassette had been carefully cleaned. The gel solution was irradiated with UV light for 10 minutes, at a distance of 10 cm from the gel. A 0.5 mm thick gel slab was obtained.

UV source: A solarium fluorescent lamp "TL/09 R" (Philips) emitting between 300–400 nm.

The gel obtained was used in the automated DNA sequencing equipment mentioned above. A standard sequencing protocol was used on M13mp18 (+) with M13 universal primer. The fragments were labelled with a fluorescent label. The sample was run in four different reactions (one for each nucleotide A, C, G and T) and the same label was used for all nucleotides. The four reaction solutions were loaded abreast on the gel. The fragments were detected by means of a laser and the collected data was transformed by computer means and presented in the form of a chromatogram. The electrophoresis was run at the following values:

U(max)=1500 V, I(max)=60 mA, P(max)=25 W, T=55° C.

The interval between collected data was 1 point/2 s and the data collecting time was 800 min.

Example 2

As a comparison chemically initiated gels were made accordingly:

The following components were mixed:
29 g urea
16 ml monomer stock solution from example 1
water (of high purity degree) to obtain 60 ml.
To this mixture were added:
8 ml buffer solution as in example 1
water (of high purity degree) to obtain 80 ml. After carefully mixing
40 μl tetramethylenediamine
400 μl ammoniumpersulfate
are added and the mixture is carefully shaken. A casette of the same type as in example 1 was quickly filled with the solution. The solution was allowed to polymerize for 90 minutes. The obtained gel was 0.5 mm and used in the same manner as in example 1.

Besides the advantages at the production of gels with the photoinitiated polymerization, the gels obtained by photopolymerization result in chromatogram with a constant distance between the peaks and a reading lenght of 650–700 bases compared with only 500 bases for the chemically initated gels. The signal/noise ratio was better for the photopolymerized gels. With the photopolymerization method it is also possible to obtain reproducible results, i.e. the same result from one run to another.

Example 3

Instead of separating DNA sequencing products this example was run on SSCP (single stranded conformation polymorphism). SSCP is another common DNA analysis method where DNA fragments are separated on non denaturing gels which are run under low temperatures. Gels for SSCP analysis were prepared accordingly:

A monomer Stock Solution:
29.7 g acrylamide
0.3 g bis-acrylamide
water (of high purity degree) to obtain 100 ml.
Buffer Solution:
0.89M Tris (107.7 g)
0.89M Boric acid (55 g)
20 mM EDTA (7.55 g)
water (of high purity degree) to obtain 1000 ml.
Running Buffer:
200 ml buffer solution.
water (of high purity degree) to obtain 2000 ml.
The following components were mixed:
16.3 ml monomer stock solution
7 ml buffer solution
45.3 ml water of high purity degree
1.4 ml initiator solution from example 1.

A cassette of the same type as in example 1 was filled with the solution. The gel solution was irradiated with UV light for 10 minutes, at a distance of 10 cm from the gel. The obtained gel was 0.5 mm thick and had a separation distance of 200 mm.

UV source: A solarium fluorescent lamp "Performance 40 W" (Philips) emitting between 300–400 nm.

The gel obtained was used in the automated DNA sequencing equipment mentioned above. In order to keep a low running temperature, additional cooling equipment was used (Multitemp®III and Cooler Kit (adaptor for connecting an external thermostat bath, multitemp) from Pharmacia Biotech, Uppsala).

Samples:
P53 fragments labelled with a fluorescent label.
Samples 1–5 are 128 bp long.
Samples 6–10 are 202 bp long.
Sample Preparation:
Denaturing solution
1.0 ml formamide
0.01% bromphenol blue.
The samples were denatured by mixing
1.5 μl of the P53 sample
3.0 μl water of high purity degree
4.5 μl denaturing solution.

The samples were equilibrated for 4 minutes at 95° C. and quickly placed on ice/water bath. The samples were allowed to cool for a few minutes before applied to the gel. The run was started immediately.

The fragments were detected by means of a laser and the collected data was transformed by computer means and presented in the form of a chromatogram. The electrophoresis was run at the following values:

U(max)=1000 V, I(max)=40 mA, P(max)=35 W, T=18° C.

The interval between collected data was 1 point/2 s and the data collecting time was 800 min.

The UV-polymerized gel gave similar separation pattern as chemically polymerised gels. All samples could be classified correctly. The UV-polymerized polyacrylamide gel proved to be well suited for SSCP separations.

Example 4

As a comparison, four of the initiator systems in EP 169 397 were investigated with respect to absorbance in the exitation area 300–350 nm:

Initiator Systems:
0.025% (w/v) Methylene blue+1% (w/v) Sodium-toluen-4-sulfinate.
0.025% (w/v) New Methylene blue+1% (w/v) Sodium-toluen-4-sulfinate.
0.1% (w/v) Sodium-1,2-naphtoquinone-4-sulfonate+1% (w/v) Sodium-toluen-4-sulfinate.
8.9 mM Benzoin methyl ether+10% ethanol.
Initiator solution from example 1, diluted to 2 mM with water of high purity.

The initiator concentrations stated above were taken directly from EP 169 397.

In order to get a uniform gel polymerisation, which is important for all electrophoresis methods but DNA sequencing in particular, the absorbance of the initiator at 300–350 nm must not be too large. The absorbances of the four initiator solutions from EP 169 397 were meassured and compared with the absorbance of 2 mM initiator from example 1. The spectrophotometer used was a Hitachi U3000.

2 mM of the initiator from example 1 resulted in absorbances between 0.7 (300 nm) and 0.1 (350 nm).

0.025% (w/v) Methylene Blue+1% (w/v) Sodium-Toluene-4-Sulfinate

The solution had a dark blue colour. The absorbance values were between 1.2 (350 nm) and 3.6 (300 nm) which is a lot higher than the values of the initiator in example 1. The dark colour makes it unusable for laser induced sample detection.

0.025% (w/v) New Methylene Blue+1% (w/v) Sodium-Toluene-4-Sulfinate

The solution had a dark blue colour. The absorbance values were between 0.9 (350 nm) and >>6=out of range (300 nm) which is a lot higher than the values of the initiator in example 1. The dark colour makes it unusable for laser induced sample detection.

0.1% (w/v) Sodium-1,2-Naphtoquinone-4-Sulphonate

The solution was transparent but with an orange colour. The absorbance values were between 3.5 (350 nm) and 6 (300 nm) which is a lot higher than the values of the initiator in example 1. The colour makes it unusable for laser induced sample detection.

8,9 mM Benzoin Methyl Ether

According to example 2 in EP 169 397, 0.4 g Benzoin Methyl Ether is to be solvated in water and ethanol to a total volume of 200 ml <=>8.84 mM initiator solution. The solution was transparent and without colour. The absorbance values were between 1.1 (350 nm) and 3.5 (300 nm) which were higher than the absorbance values of the initiator solution in example 1.

Example 5

As a comparison, gels were prepared with 8.9 mM Benzoin Methyl Ether accordingly:

Benzoin Methyl Ether Stock Solution:

According to EP 169 397, 0.4 g Benzoin Methyl Ether is to be dissolved in 10 ml ethanol and water added to 50 ml. This was impossible due to bad solubility of Benzoin Methyl Ether in water, and the initiator was therfore dissolved in 20 ml ethanol and water to 50 ml.

The following components were mixed:

33.6 g urea, 16 ml monomer stock solution from example 1, water (of high purity degree) to obtain 40 ml.

To this mixture were added:

8 ml buffer solution from example 1, 20 ml Benzoin Methyl Ether stock solution, water (of high purity degree) to 80 ml.

After filtration the solution was poured into a gel cassette of the same type as in example 1. The gel solution was irradiated with UV light for 10 minutes, at a distance of 10 cm from the gel. A 0.5 mm thick gel slab with 200 mm separation distance was obtained.

UV source: A solarium fluorescent lamp "TL/09 R" (Philips) emitting between 300–400 nm.

Figure 2A:
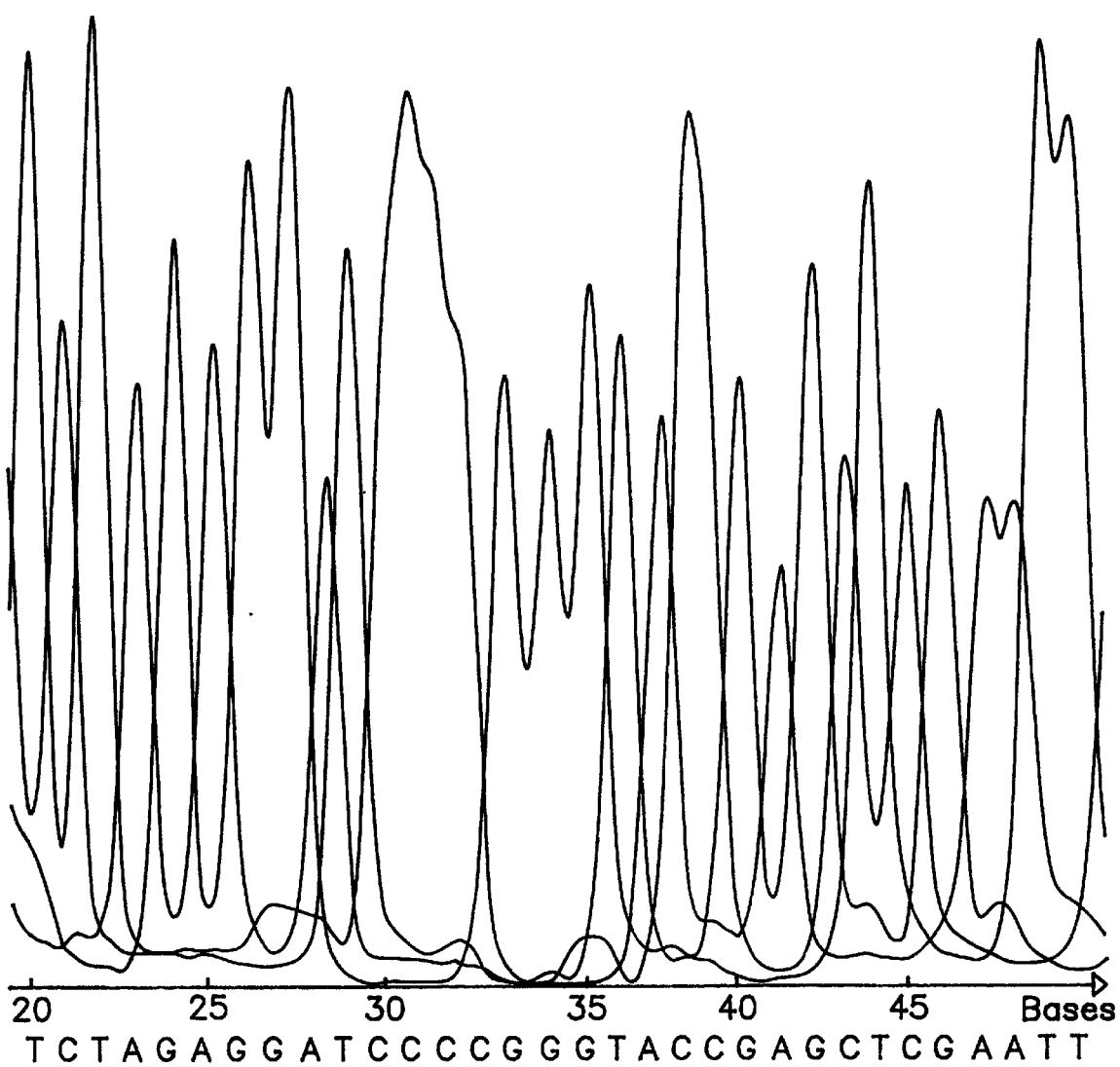
FIG. 2a represents bases in the beginning of the sequence in the gel of the prior art.
Figure 2B:
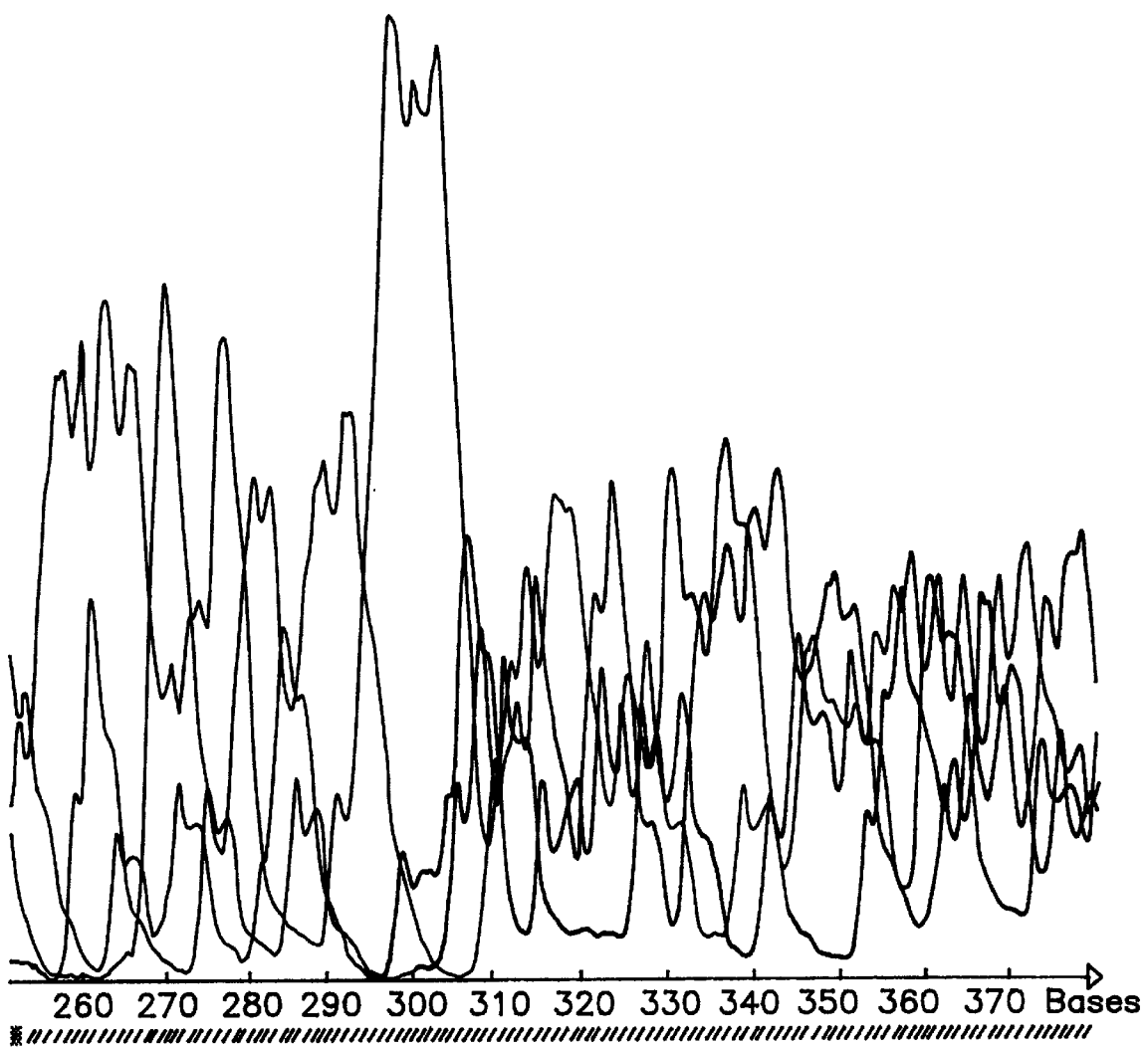
FIG. 2b represents bases further on in the sequence in the gel of the prior art.

As a comparison, another gel was prepared according to the recipe above, but with 1.6 ml initiator solution from example 1 instead of Benzoin Methyl Ether. Both gels were run in the same manner as in example 1. The results are presented in FIGS. 1a, 1b, 2a and 2b. The figures represent chromatograms from the run of the samples on the two gels. FIGS. 1a and 1b represents the gel according to the invention and FIGS. 2a and 2b represents the gel prepared according to the state of the art. In both figures, figure a represent bases in the beginning of the sequence and figure b shows bases further on in the sequence.

As is evident from the figures, early in the sequence both gels give good results, but already at 300 bases, as shown in FIG. 2b, the peaks of the Benzoin Methyl Ether gel are so distorted that it is impossible to analyse the data. On the other hand, the gel with initiator from example 1 give nicely shaped peaks that can be correctly analysed far beyond 300 bases, as can be seen in FIG. 1b. These results indicate that the gel prepared with the initiator solution from example 1 polymerises the gel much more evenly than benzoin methyl ether. (it should be noted in FIGS. 1b and 2b that it is the same position in the sequence shown, but due to the distorted data the algorithm has failed to make a correct base calling in FIG. 2b.)

We claim:

1. Method for electrophoretic separation of nucleic acid fragments comprising the following steps:

a) providing a polyacrylamide based gel prepared by photoinitiated polymerization of a mixture containing monoolefinic- and di- and/or polyolefinic monomers and a photoinitiator of the general formula:

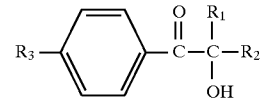

where $R_1$ and $R_2$ independently are $CH_3$, $C_2H_5$ or $C_3H_7$ or $R_1$, $R_2$ together with the carbon atom form a cycloaliphatic ring with 4–8 carbons;

$R_3$=H, $CH_3$, $C_2H_5$ or —O—$(CH_2CH_2)_n$—OH with n=1–20;

b) applying said nucleic acid fragments on said polyacrylamide based gel;

c) electrophoretically separating said fragments on said gel.

2. Method according to claim 1, wherein the photoinitiator is a compound with the formula:

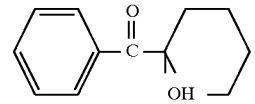

3. Method according to claim 1, wherein the initiator is a compound with the formula:

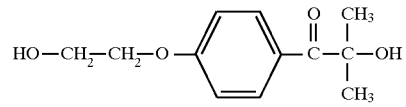

4. Method according to any of the claims 1–3, wherein the polymerization is initiated by UV light of a wave length of 300–400 nm.

5. Method according to any of the claims 1 to 3 wherein the separation is performed in automated DNA sequencing.

6. Method according to any of the claims 1 to 3 wherein the separation is performed in fluorescence based automated DNA sequencing.

7. A polyacrylamide-based gel electrophoresis kit for separating nucleic acids, the kit comprising:
(i) a mixture of monoolefinic- and di- and/or polyolefinic monomers;
(ii) optionally buffer and denaturing agent;
(iii) a photo initiator with the general formula:

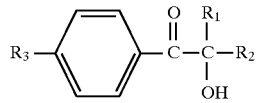

where
$R_1$ and $R_2$ independently are $CH_3$, $C_2H_5$ or $C_3H_7$ or $R_1$, $R_2$ together with the carbon atom form a cycloaliphatic ring with 4–8 carbons;
$R_3$=H, $CH_3$, $C_2H_5$ or —O—$(CH_2CH_2)_n$—OH with n=1–20.

8. A kit according to claim 7, wherein the photoinitiator is compound with the formula:

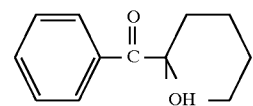

9. A kit according to claim 7, wherein the photoinitiator is a compound with the formula:

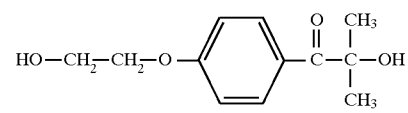

* * * * *